United States Patent
Stillinger

(10) Patent No.: US 7,908,929 B2
(45) Date of Patent: Mar. 22, 2011

(54) TEST APPARATUS

(75) Inventor: Jeffrey D. Stillinger, Indianapolis, IN (US)

(73) Assignee: Rolls-Royce Corporation, Indianapolis, IN (US)

( * ) Notice: Subject to any disclaimer, the term of this patent is extended or adjusted under 35 U.S.C. 154(b) by 27 days.

(21) Appl. No.: 12/286,201

(22) Filed: Sep. 29, 2008

(65) Prior Publication Data

US 2010/0077871 A1 Apr. 1, 2010

(51) Int. Cl.
*G01N 3/02* (2006.01)

(52) U.S. Cl. .......................................... 73/856; 73/760

(58) Field of Classification Search ............... 73/760, 73/856
See application file for complete search history.

(56) References Cited

U.S. PATENT DOCUMENTS

| | | | |
|---|---|---|---|
| 3,693,424 A | 9/1963 | Barnet et al. | |
| 3,111,840 A | 11/1963 | Barnet et al. | |
| 3,792,608 A | 2/1974 | Holm et al. | |
| 3,919,884 A * | 11/1975 | Gunderson et al. | 73/831 |
| 3,934,464 A | 1/1976 | McCauley | |
| 4,358,961 A | 11/1982 | Woods, Jr. | |
| 4,425,802 A | 1/1984 | Sponseller | |
| 4,433,473 A * | 2/1984 | Benedetti | 29/598 |
| 4,607,426 A * | 8/1986 | Kelly | 29/421.1 |
| 4,629,011 A * | 12/1986 | Reinhardt | 175/58 |
| 4,716,767 A | 1/1988 | Krawchuk | |
| 4,904,137 A * | 2/1990 | Matuschek | 411/501 |
| 5,097,689 A * | 3/1992 | Pietrobon | 72/58 |
| 5,226,308 A | 7/1993 | Gibson | |
| 5,880,374 A * | 3/1999 | MacKarvich | 73/804 |
| 6,139,414 A * | 10/2000 | Domanski et al. | 451/471 |
| 6,810,751 B2 | 11/2004 | Moreno et al. | |
| 7,051,600 B1 * | 5/2006 | Cavallaro et al. | 73/862.041 |
| 7,451,661 B2 * | 11/2008 | Burton et al. | 73/850 |
| 7,533,557 B1 * | 5/2009 | Mott et al. | 73/12.14 |
| 2002/0049447 A1 * | 4/2002 | Li | 606/73 |
| 2002/0162400 A1 | 11/2002 | Xie et al. | |
| 2004/0016301 A1 | 1/2004 | Moreno et al. | |

\* cited by examiner

*Primary Examiner* — Max Noori
(74) *Attorney, Agent, or Firm* — Krieg DeVault LLP

(57) ABSTRACT

One embodiment of a testing device is disclosed having an expansible element that expands radially outwardly upon the application of an axial force. In one form the testing device includes two bellows forming a deflection surface that expands radially outward upon the application of axial force to the testing device.

17 Claims, 3 Drawing Sheets

TEST APPARATUS

TECHNICAL FIELD

The present inventions relates generally to test systems, and more particularly, but not exclusively, to test systems capable of generating radial and hoop stresses in a test article.

BACKGROUND

The generation of radial and hoop stresses in annular-like components remains an area of interest for the efficient testing of, among other things, gas turbine engine components. Some existing systems have various shortcomings, drawbacks, and disadvantages relative to certain applications. Accordingly, there remains a need for further contributions in this area.

SUMMARY

One embodiment of the present invention is a unique method of applying radial and hoop stresses. Other embodiments include unique apparatus, systems, devices, hardware, methods, and combinations for the generation of radial and hoop stresses. Further embodiments, forms, features, aspects, benefits, and advantages of the present application shall become apparent from the following description and drawings.

DETAILED DESCRIPTION OF REPRESENTATIVE EMBODIMENTS

Figure 1:
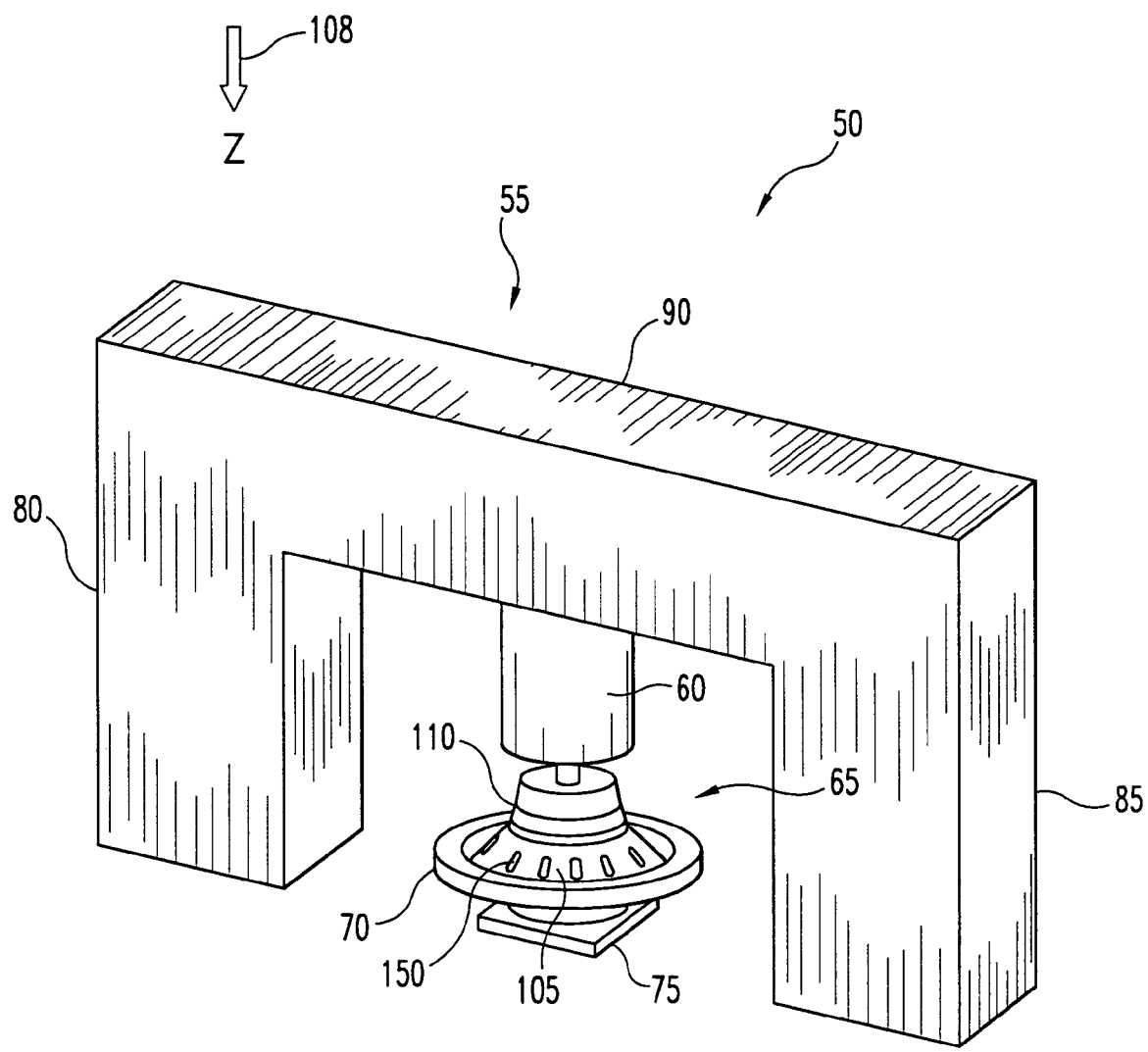
FIG. 1 is a perspective view of one embodiment of a testing device disposed in a system.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
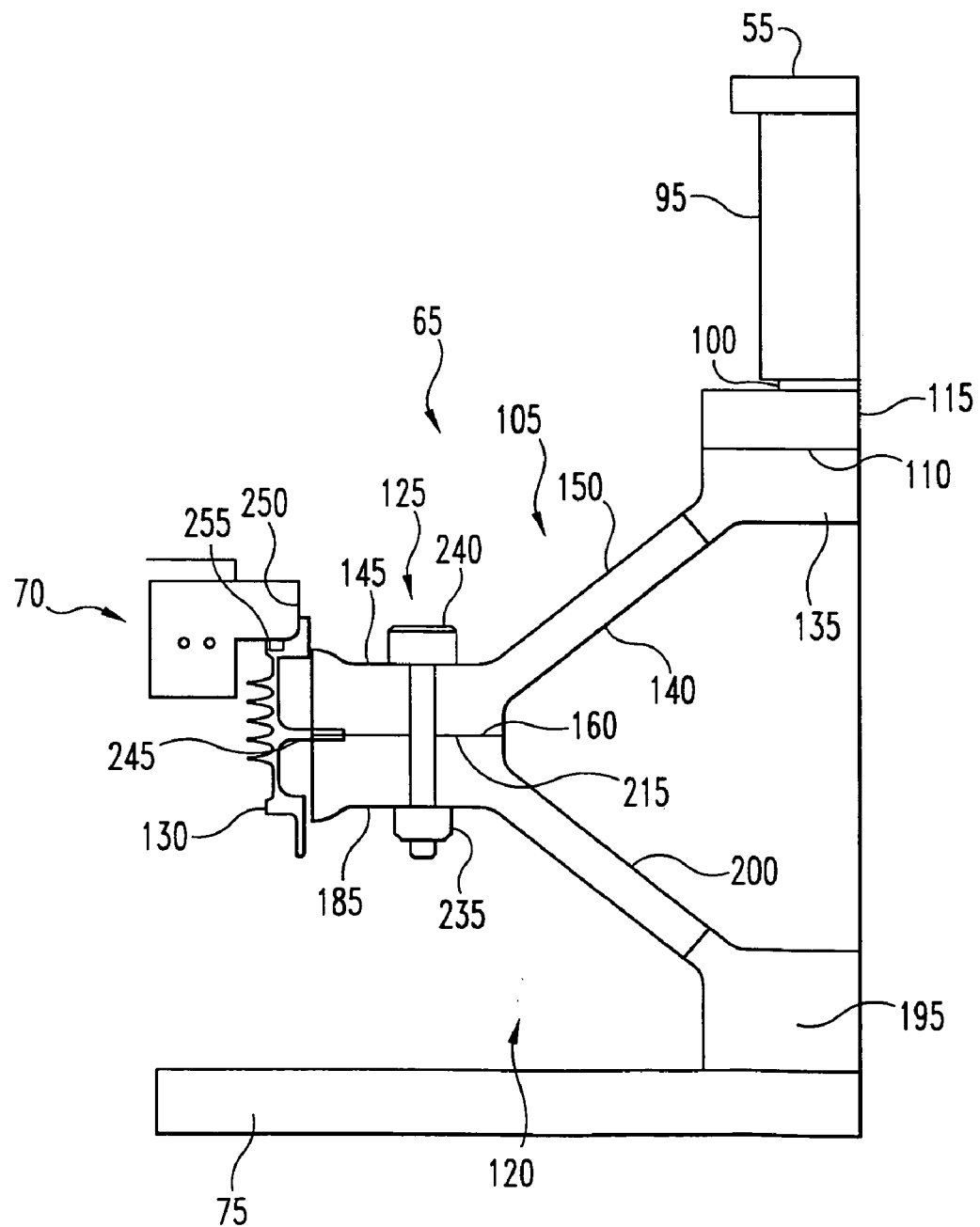
FIG. 2 is a partial side view of one embodiment of a testing device disposed in a test system.

Referring to FIGS. 1 and 2, one form of a test system 50 is shown having a support structure 55, an actuator 60, a testing device 65, a support ring 70, and a pad 75. The test system 50 is useful in applying circumferentially distributed loads that are directed radially outward to a test article (not shown) and does this by imparting a load having an axial component into the testing device 65 to create radial deflections. In some embodiments, however, the load may further include off-axis loading components. Some embodiments of the testing device 65 may be easy to disassemble and in some cases, penetrant inspection can be done without disassembly.

In one form the support structure 55 is constructed with support beams 80 and 85 and a loading beam 90. The support structure 55 is constructed to accommodate the loads necessary to conduct a range of tests and may have a sufficiently long fatigue life such as would be suitable to support multiple test cycles. Various types of structural configurations are contemplated for the support beams 80 and 85 and the loading beam 90. For example, the loading beam 90 can take the form of an I-beam. In addition, each beam can be comprised of numerous structural components or can be solid. The beams can be attached to one another using bolted or welded connections and, furthermore, can be composed of a variety of materials. In one form, the support beams 80 and 85 and the loading beam 90 are formed as an integral assembly, but in other forms can be unitary. In another form, the support structure 55 may be triangular such that two lateral, opposing support beams support the testing device 65 at the apex of the triangle.

In one form the actuator 60 includes an actuator body 95 and an actuation member 100 and is releasably attached to the loading beam 90, but in some embodiments may be permanently attached to the support structure 55. In other embodiments, the actuator 60 can be attached to the support beams 80 or 85. The actuation member 100 is used to supply a force generated by the actuator 60 in at least an axial direction and can be sized to provide a broad range of forces at varying actuation rates to suit a particular test article and testing regime. The actuator 60 is hydraulic in the illustrative embodiments but in some forms may be pneumatic, piezoelectric, or electromechanical, to name just a few non-limiting examples. In some embodiments, more than one actuator can be attached to the support structure 55 to conduct a single test, or alternatively a series of actuators can be supplied to conduct multiple simultaneous tests within the support structure 55.

The testing device 65 in one form includes a first bellows 105, a second bellows (not shown) and the support ring 70. The first bellows 105 can be constructed of a rigid material, such as metal, is circular in shape, and includes apertures or slots formed therein. The first bellows is operable to produce a radially outward expansion upon the application of the axial force in a z-direction 108 to the first bellows 105. The first bellows 105 includes a circumferential periphery. The support ring 70 substantially surrounds the circumferential periphery of the first bellows 105 and can provide a surface on which the test article (not shown) is partially supported. Further information regarding the structural details of the first bellows 105 and the second bellows (not shown) as well as the relative orientation of the support ring 70 to the test article (not shown) is provided further below. The first bellows 105 includes a force application region 110 configured to receive an axial force imparted by the actuation member 100. In some embodiments, the actuation member 100 directly contacts the force application region 110 to impart the axial force.

The second bellows (not shown) can be oriented below the first bellows 105 and in some forms provide a mirror image to the first bellows 105. In some embodiments, however, the second bellows (not shown) need not form the mirror image of the first bellows 105. Further details of the second bellows may be seen in FIGS. 2 and 3 and is described further below.

The support ring 70 is configured to be received around the first bellows 105 and can be used to provide support to the test article (not shown) disposed between the first bellows 105 and the support ring 70. The support ring 70 is formed as a unitary member but in other embodiments can be composed of an assembly of parts. The support ring 70 is placed into contact with the test article (not shown). In one form, the support ring 70 can be at least partially attached or integrally formed with the first bellows 105 or the second bellows (not shown). Some embodiments may not need a support ring.

A pad 75 can be located beneath the testing device 65 opposite the actuator 60. When the actuator 60 imparts an axial force to the force application region 110, the pad 75 generates an equal and opposite force such that the testing device 65 remains somewhat stationary except primarily for deflections caused by the application of force, whether or not that force is predominantly in the axial direction. In some forms, however, the pad 75 can be somewhat non-stationary. The pad 75 can be formed of any suitable material, can take on a variety of forms, and can, but need not be, integrated with the support structure 55.

Figure 3:
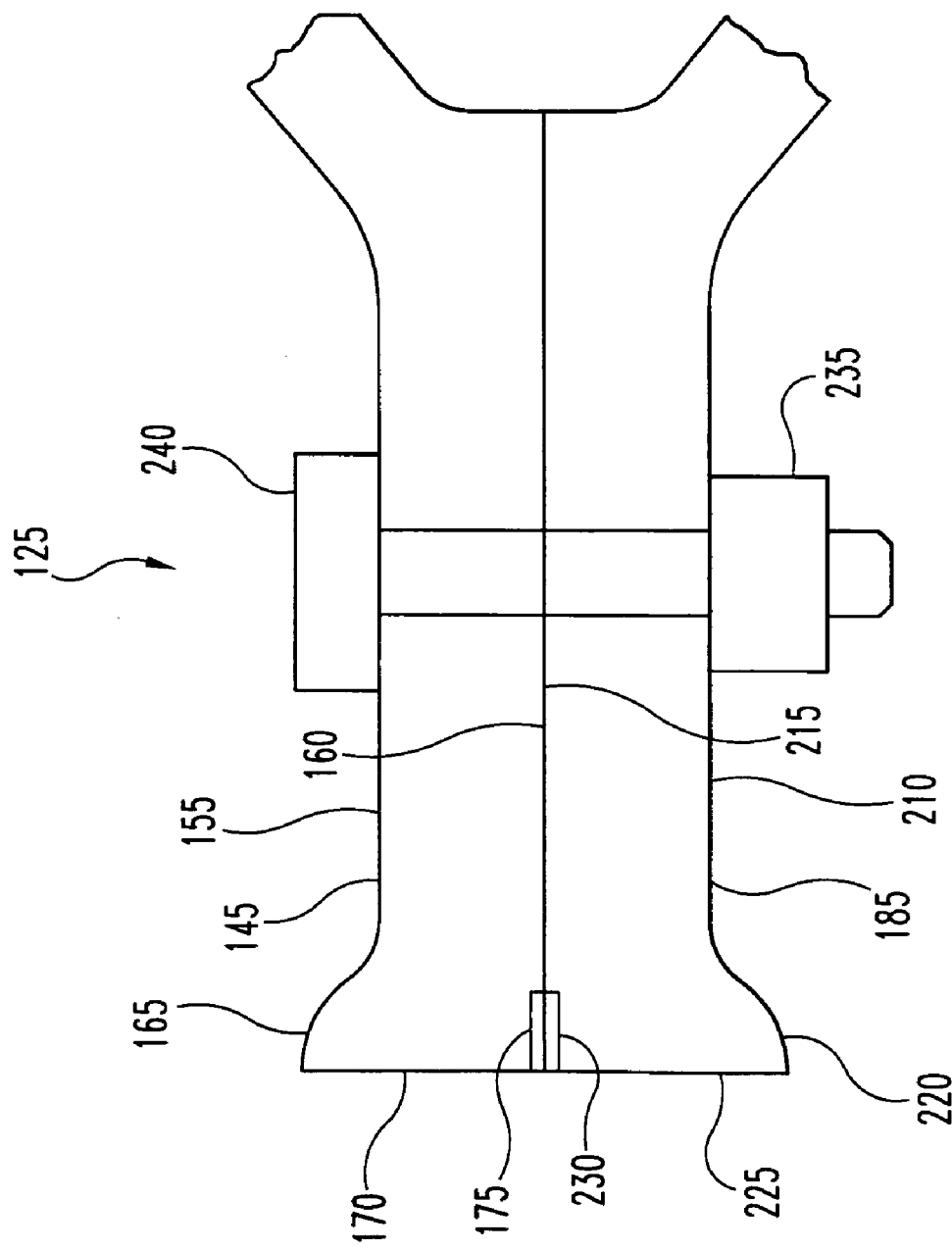
FIG. 3 is a partial side view of one embodiment of a testing device.

Referring now FIGS. 2 and 3, wherein like numerals refer to like elements, a cross-sectional view of one embodiment of the testing device 65 is shown. The testing device 65 is shown as located between the actuator 60 and a spacer 115 on one side and the pad 75 on the other. In one form the testing device 65 includes the first bellows 105, a second bellows 120, and a bellows connector 125 and is used to convert axial force applied to the testing device 65 into radial and hoop stresses within a test article 130. As used herein, the term bellows can include any rigid or semi-rigid structure that radially expands upon the application of axial force.

In one form the first bellows 105 includes a first cap 135, a first reactive member 140, and a first bellows flange 145. The first cap 135 includes the force application region 110 which receives axial force from the actuation member 100 through the spacer 115. In some embodiments, however, the spacer 115 may not be present and the force application region 110 may receive axial force directly from the actuation member 100. The first cap 135 can be comprised of metal or any other suitable material. The first cap 135 is configured to support a wide range of forces imparted by the actuation member 100.

The first reactive member 140 is connected to the first cap 135 and is made of any suitable material that reacts and suitably deflects upon application of a force to the force application region 110. The first reactive member 140 is formed as frustum-conical in shape and extends away from the first cap 135. The first reactive member 140 can take different shapes in other embodiments. The first reactive member 140 can be connected to the first cap 135 through a variety of mechanisms or, alternatively, can be formed as a unitary part as depicted in the illustrated embodiment. In one form the first reactive member 140 includes slots 150 that are configured to provide the first reactive member 140 with reactive deflections. The slots 150 are formed as ovals into the first reactive member 140, but in other embodiments may take forms such as, but not limited to, rectangles, squares, triangles, and teardrops. The slots 150 may not be symmetric in some embodiments. The ovals depicted in the embodiment of FIG. 1 can be arranged having a long axis extending from the first cap 135 to the first bellows flange 145, or any other orientation. The slots 150 can be any structural arrangement that is, in the broadest sense, formed in any way that allows the first reactive member 140 to deflect upon the application of the axial force to the first bellows 105. In some embodiments, multiple slots 150 of varying shapes, configurations, and orientations can be formed in the first reactive member 140.

In one form the first bellows flange 145 includes a first flange member 155, a first flange interface 160, a first flange cusp 165, a first flange abutment 170, and a first flange slot 175. The first bellows flange 145 is formed or attached to the first bellows 105 and the first reactive member 140. Alternatively, the first bellows flange 145 can be connected to the first reactive member 140 using a variety of techniques. The first bellows flange 145 provides a suitable surface to connect to other structural components of the testing device 65. For example, the first bellows flange 145 can be made of a rigid material suitable to withstand forces generated during a test.

In the illustrated embodiment, the first bellows flange 145, the first reactive member 140, and the first cap 135 are formed of metal, but other materials are also contemplated, such as high-strength plastic.

The first flange member 155 extends from the first reactive member 140 and is configured to support a portion of the bellows connector 125. The first flange member 155 can extend at any angle from the first reactive member 140.

In one form the first flange interface 160 is included in the first bellows flange 145 and provides a suitable surface in which to interface with a second bellows flange 185, discussed further hereinbelow. The first flange interface 160 can be a flat surface in the illustrated embodiment, but other surfaces are also contemplated, such as a saw-tooth surface, to set forth one non-limiting example.

The first flange cusp 165 is formed in the first bellows flange 145 and provides a suitable extension to the first bellows flange 145. In some embodiments the first flange cusp 165 can be separately formed and subsequently attached to the first bellows flange 145. The first flange cusp 165 can be any size, and in some embodiments might not be present at all. The first flange cusp 165 is shown as a curvilinear shape in the illustrated embodiments, but other shapes are also contemplated such as a straight line.

The first flange abutment 170 is provided to interface to the test article 130 and is shown having a flat surface in the illustrated embodiment. Other configurations are also contemplated for the first flange abutment 170, including, but not limited to, a curvilinear shape.

In one form the first flange slot 175 is formed in the first bellows flange 145 and is configured to accept a portion of the test article 130. The first flange slot 175 can be cut, milled, or molded into the first bellows flange 145 and can be any size or configuration. The first flange slot 175 is shown as an elongate slot cut from the first flange abutment 170 towards the first reactive member 140 and can have any suitable dimensions. The first flange slot 175 can be rectangular, circular, or any other type of shape. In some embodiments, the first flange slot 175 need not be formed in the first bellows flange 145.

In one form the second bellows 120 includes a second cap 195, a second reactive member 200, and the second bellows flange 185. The second cap 195 includes a force application region which receives axial force from the pad 75. In some embodiments, a spacer can be present between the second cap 195 and the pad 75. The second cap 195 can be comprised of metal or any other suitable material. The second cap 195 is configured to support a wide range of forces.

The second reactive member 200 is connected to the second cap 195 and is made of any suitable material that reacts and suitably deflects upon application of a force to the force application region 110. The second reactive member 200 is formed as frustum-conical in shape and extends away from the second cap 195. The second reactive member 200 can take different forms in other embodiments. The second reactive member 200 can be connected to the second cap 195 through a variety of mechanisms or, alternatively, can be formed as unitary part as depicted in the illustrated embodiment. In one form the second reactive member 200 includes slots 150 that are configured to provide the second reactive member 200 with reactive deflections. The slots 150 are formed as ovals into the second reactive member 200, but in other embodiments may take forms such as, but not limited to, rectangles, squares, triangles, and teardrops. The slots 150 may not be symmetric in some embodiments. The ovals depicted in the embodiment of FIG. 1 can be arranged having a long axis extending from the second cap 195 to the second bellows flange 185, or any other orientation. The slots 150 can be any structural arrangement that is, in the broadest sense, formed in any way that allows the second reactive member 200 to deflect upon the application of axial force to the second bellows 120. In some embodiments, multiple slots 150 of varying shapes, configurations, and orientations can be formed in the second reactive member 200.

In one form the second bellows flange 185 includes a second flange member 210, a second flange interface 215, a second flange cusp 220, a second flange abutment 225, and a second flange slot 230. The second bellows flange 185 is formed or attached to the second bellows 120 and the second reactive member 200. Alternatively, the second bellows flange 185 can be connected to the second reactive member 200 using a variety of techniques. The second bellows flange 185 provides a suitable surface to connect to other structural components of the testing device 65. For example, the second bellows flange 185 can be made of a rigid material suitable to withstand forces generated during a test. In the illustrated embodiment, the second bellows flange 185, the second reactive member 200, and the second cap 195 are formed of metal, but other materials are also contemplated, such as high-strength plastic.

The second flange member 210 extends from the second reactive member 200 and is configured to support a portion of the bellows connector 125. The second flange member 210 can extend at any angle from the second reactive member 200.

In one form the second flange interface 215 is included in the second bellows flange 185 and provides a suitable surface in which to interface with the first bellows flange 145, discussed previously herein. The second flange interface 215 can be a flat surface in the illustrated embodiment, but other surfaces are also contemplated, such as a saw-tooth surface, to set forth one non-limiting example.

The second flange cusp 220 is formed in the second bellows flange 185 and provides a suitable extension to the second bellows flange 185. In some embodiments the second flange cusp 220 can be separately formed and subsequently attached to the second bellows flange 185. The second flange cusp 220 can be any size, and in some embodiments might not be present at all. The second flange cusp 220 is shown as a curvilinear shape in the illustrated embodiments, but other shapes are also contemplated such as a straight line.

The second flange abutment 225 is provided to interface to the test article 130 and is shown having a flat surface in the illustrated embodiment. Other configurations are also contemplated for the second flange abutment 225, including, but not limited to, a curvilinear shape.

In one form the second flange slot 230 is formed in the second bellows flange 185 and is configured to accept a portion of the test article 130. The second flange slot 230 can be cut, milled, or molded into the second bellows flange 185 and can be any size or configuration. The second flange slot 230 is shown as an elongate slot cut from the second flange abutment 225 towards the second reactive member 200 and can have any suitable dimensions. The second flange slot 230 can be rectangular, circular, or any other type of shape. In some embodiments, the second flange slot 230 need not be formed in the second bellows flange 185.

In the illustrated embodiment, the first bellows 105 and the second bellows 120 are similarly formed, but in some embodiments may take different forms. For example, the first bellows 105 can have greater or fewer slots 150 than the second bellows 120; the first bellows 105 might not have the first flange slot 175 while the second bellows 120 has the second flange slot 230; or the first bellows 105 can have a different relative orientation between the first reactive member 140 and the first bellows flange 145 to set forth a few non-limiting examples. It will be understood that any variety of configurations are possible so long as axial force applied to testing device is converted at least in part to radial and hoop stresses within the test article 130.

The bellows connector 125 is used to connect the first bellows 105 to the second bellows 120 and, in the illustrated embodiment, comprises a nut 235 and a bolt 240. An aperture is formed in both the first bellows flange 145 and the second bellows flange 185 which allows the bolt 240 to pass through and connect the first bellows 105 to the second bellows 120. The nut 235 is turned and tightened to secure the first bellows flange 145 to the second bellows flange 185 to create the integrated testing device 65. In other embodiments, apertures might not be provided in the first bellows flange 145 or the second bellows flange 185 such that the bellows connector 125 may have another form, such as a welded joint. Therefore it will be understood that the bellows connector 125 can have any number of forms such as, but not limited to, bolted, riveted, welded, and clamped. The test article 130 is shown in the illustrated embodiment as disposed between the first bellows flange 145 and the second bellows flange 185. The test article 130 can be any number of components, such as gas turbine engine components, and are generally annular in shape. In some embodiments, however, the test article 130 might not be annular in shape but rather might have a multi-faceted appearance. In one form the test article 130 includes a test article stub 245 which extends from the test article 130 and is used in the testing environment to be secured between the first bellows flange 145 and the second bellows flange 185 such that when the nut 235 is turned and tightened to the bolt 240, the first bellows flange 145 and the second bellows flange 185 forms a sandwich and secures the test article 130 into place. A groove or cutout in the form of the first flange slot 175 and the second flange slot 230 can be provided to accommodate the test article stub 245. In some embodiments, the test article 130 might not include the test article stub 245 and might instead have a smooth inner surface that allows the test article 130 to be press fit over the first bellows flange 145 or the second bellows flange 185. In these embodiments, it may not be necessary to have the first flange slot 175 or the second flange slot 230.

In one application, the support ring 70 is used to provide a support surface on which the test article 130 is connected. The support ring 70 in one form includes a support ring first surface 250 and a support ring second surface 255. The support ring 70 can be formed of any material suitable to withstand forces generated during a test of the test article 130 and can have any number of surfaces that are arranged in any number of orientations necessary to support the test article 130. However, in some embodiments the support ring 70 may not be needed.

In one form of operation, the first bellows 105 and the second bellows 120 is placed between the actuator 60 and the pad 75. When the actuator 60 forces the actuation member 100 into contact with the spacer 115 and applies an axial force, the equal and opposite reactive force generated from the pad 75 forces the first cap 135 and the second cap 195 to move closer relative to each other thereby moving the first reactive member 140 and the second reactive member 200 and creating a radial and hoop stress in the test article 130 as the first bellows flange 145 and the second bellows flange 185 push radially outward on the test article 130.

Other embodiments are also contemplated. For example, the pad that the testing device rests upon may be integrated into the support structure. In this embodiment the support structure can have a square, rectangular, circular, or other shape as would allow the pad to be integrated into the loading beam and support beam arrangement.

In another embodiment, the first bellows and the second bellows may have an unequal number of apertures. In addition, the apertures between the bellows need not have the same geometry.

In yet another embodiment, the testing device may have only one bellows, wherein the bellows is located between the actuator and the pad and wherein axial force applied by the actuator is converted to radial and hoop stresses within the test article. In such an embodiment, the testing device may have the form similar to the first bellows or the second bellows. Other forms are also contemplated herein.

In yet other embodiments, the bellows need not be circular in shape, but rather can have the first flange abutment surface that is faceted. Furthermore, the first reactive surface need not be conical in shape, but could also be faceted.

In a further embodiment, a testing apparatus is provided which includes a reactive device having an expansible element with a circumferential outer surface, wherein the expansible element is capable of moving from a rigid first position to a rigid second position upon application of an axial external force, wherein the circumferential outer surface extends radially outward when the external force is applied, and wherein the outward extension of the reactive device imparts a force to a test article.

In one embodiment of the present application, a testing device is disclosed that is capable of expanding radially outward upon the application of axial force. In one form the testing device includes a first bellows and a second bellows, each having apertures formed therein. The first bellows and the second bellows have a generally conical shape and may be joined together at their respective bases. An annular test article is placed around the region in which the first bellows and the second bellows are joined. When axial force is applied, the first bellows and the second bellows may expand radially outward thus providing radial and hoop stress to the test article.

In yet another embodiment, an apparatus is provided comprising a radial expansion test device having a first bellows including a force application region, the first bellows coupled to a second bellows including a support surface, the first bellows and the second bellows forming an outer force applicator structure operable to expand radially outward when a force is applied to the force application region of the first bellows.

In still another embodiment, an apparatus is provided comprising a test rig force applicator having a deformable first structure, a deformable second structure, and an annular reactive middle member disposed between an end of the first structure and an end of the second structure and the annular reactive middle surface moves outwardly to transmit an outwardly directed force to an article when the deformable structures are expanded by application of force having an axial component to the test rig force applicator.

In still another embodiment, an apparatus is provided comprising a test device arranged along an axis and having a periphery that circumscribes the axis, the periphery operable to be deflected radially outward when the test device is acted upon by a force having a component along the axis and means for producing a radial outward deflection of the periphery when the test device is acted upon by the force.

In yet another embodiment, a test method is provided comprising applying an axial force to a force application region of a testing device, decreasing an axial distance between a first reactive device and a second reactive device of the testing device, converting the axial force to a radial deflection, and generating radial and hoop stress within a test article.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. An apparatus comprising:
 a radial expansion test device having a first bellows including a force application region, the first bellows coupled to a second bellows including a support surface, the first bellows and the second bellows forming an outer force applicator structure operable to expand radially outward when a force is applied to the force application region of the first bellows.

2. The apparatus of claim 1, wherein the first bellows and the second bellows are releasably coupled.

3. The apparatus of claim 1, wherein the first bellows and the second bellows are mirror images.

4. The apparatus of claim 1, wherein the first bellows has a plurality of apertures formed therein.

5. The apparatus of claim 1, wherein the outer force applicator structure includes a circumferential surface.

6. The apparatus of claim 1, which further includes a support ring enclosing the outer force applicator structure.

7. The apparatus of claim 1, wherein the outer force applicator structure includes an opening, the opening operable to engage a test component.

8. The apparatus of claim 1, which further includes a test rig having a support structure and a pad, wherein the support surface of the second bellows is located between the pad and the support structure.

9. The apparatus of claim 8, which further includes an actuator coupled to the test rig; wherein the actuator is operable to transmit the force to the force application region of the first bellows such that the outer force applicator structure moves outwardly when the actuator imparts a force to the force application region.

10. The apparatus of claim 1, which further includes a test rig having a support structure and a pad, wherein the support surface of the second bellows engages the pad; which further includes an actuator coupled to the test rig; wherein the actuator is operable to transmit the force to the force application region of the first bellows such that the outer force applicator structure moves outwardly when the actuator imparts a force to the force application region; wherein the first bellows and the second bellows are releasably coupled; wherein the first bellows and the second bellows are mirror images; and wherein the first bellows has a plurality of apertures formed therein.

11. The apparatus of claim 1, wherein the outer force applicator structure includes a circumferential surface; which further includes a support ring enclosing the outer force applicator structure; wherein the outer force applicator structure includes an opening, the opening operable to engage a test component.

12. An apparatus comprising:
a test rig force applicator having a deformable first structure, a deformable second structure, and an annular reactive middle member disposed between an end of the first structure and an end of the second structure;
the annular reactive middle member moves outwardly to transmit an outwardly directed force to an article when the deformable structures are expanded by application of force having an axial component to the test rig force applicator; and
wherein the deformable first structure is a bellows and the deformable second structure is a bellows.

13. The apparatus of claim 12, wherein the deformable first structure and the deformable second structure have an identical shape.

14. The apparatus of claim 13, which further includes a test rig having an actuator operable to apply force to the deformable structures.

15. The apparatus of claim 12, wherein a connection of an outer periphery of the deformable first structure and an outer periphery of the deformable second structure form the annular reactive middle surface.

16. A test method comprising:
applying an axial force to a force application region of a testing device;
decreasing an axial distance between a first reactive device and a second reactive device of the testing device;
converting the axial force to a radial deflection; and
generating radial and hoop stress within a test article; and
cycling the axial force to complete a testing program.

17. The method of claim 16, which further includes inspecting the test article at a conclusion of the testing program.

* * * * *